United States Patent [19]

Castaman et al.

[11] Patent Number: 4,745,913
[45] Date of Patent: May 24, 1988

[54] APPARATUS FOR THE STABILIZATION OF BONE FRACTURES

[76] Inventors: Enrico Castaman, Contra S. Bortolo 59; Lino Borghettino, Via Battaglione Aosta 14, both of Vicenza 1-36100, Italy

[21] Appl. No.: 885,570
[22] PCT Filed: Nov. 7, 1985
[86] PCT No.: PCT/IT85/00045
 § 371 Date: Jun. 24, 1986
 § 102(e) Date: Jun. 24, 1986
[87] PCT Pub. No.: WO86/02822
 PCT Pub. Date: May 22, 1986

[30] Foreign Application Priority Data
 Nov. 8, 1984 [IT] Italy .................... 85660 A/84

[51] Int. Cl.⁴ .................................. A61B 17/60
[52] U.S. Cl. ................... 128/92 ZW; 128/92 YQ; 128/92 Z; 128/92 ZK; 128/92 YP
[58] Field of Search .......... 128/92 YQ, 92 ZW, 92 Z, 128/92 ZK, 92 YP

[56] References Cited

U.S. PATENT DOCUMENTS

| 1,789,060 | 1/1931 | Weisenbach | 128/92 Z |
| 2,435,850 | 2/1948 | Siebrandt | 128/92 Z |
| 2,439,995 | 4/1948 | Thrailkill | 128/92 ZW |
| 4,261,350 | 4/1981 | Branemark et al. | 128/92 YQ |
| 4,393,868 | 7/1983 | Teague | 128/92 ZW |

FOREIGN PATENT DOCUMENTS

| 203544 | 6/1939 | Switzerland | 228/92 Z |
| 935093 | 8/1980 | U.S.S.R. | 128/92 ZW |

*Primary Examiner*—C. Fred Rosenbaum
*Assistant Examiner*—Colleen Reilly
*Attorney, Agent, or Firm*—Bucknam and Archer

[57] ABSTRACT

The external device for fixing the pins to be inserted into the bone fragments comprises at least one carrier bar, a screw for securing the pins to the carrier bar, a stirrup and a washer for securing the screw to the carrier bar. The stirrup and the washer have at least on the surfaces in contact with the rough surfaces of the bar a deformable lining. The device permits the adjustment of the different parts and improved stabilization of the pins.

6 Claims, 4 Drawing Sheets

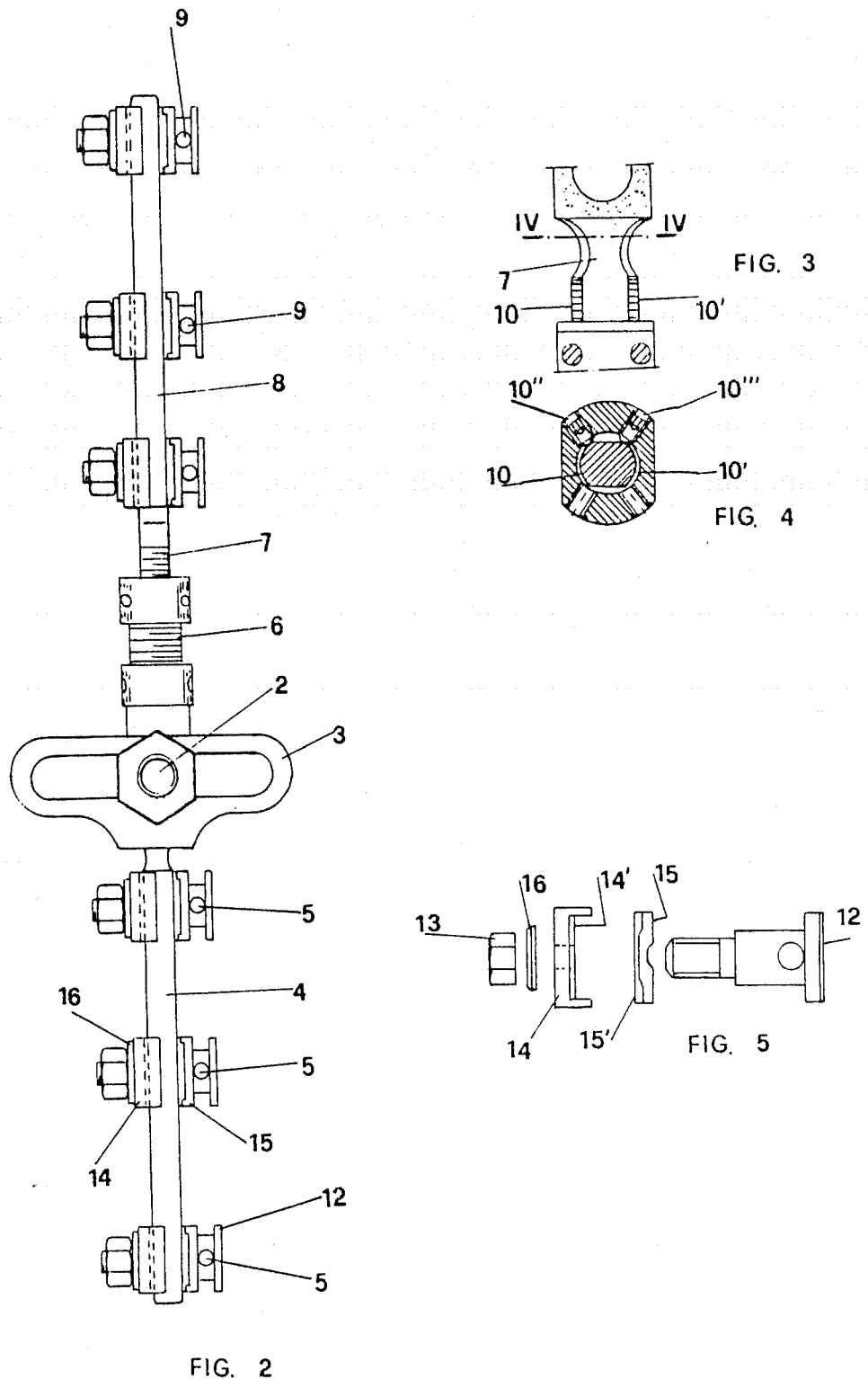

APPARATUS FOR THE STABILIZATION OF BONE FRACTURES

DESCRIPTION

The present invention has for its object to provide an apparatus for the stabilization of bone fractures.

It is known at this time that the problem of stabilization with mechanical means of bone fractures, as a substitute for the more cumbersome, obsolete and non functional plaster casting, has been tackled by various surgical teams in the principal countries of the world.

At the end of 1942 Otto Stader in the United States (U.S. Pat. No. 2,393,831) proposed to fix the fracture of long bones by means of transosseous nails which however had a considerable weight and a lack of utility in use, in that they did not permit to reduce the fracture in separate frontal and sagittal planes to put in correct alignment the two damaged bones to be joined together. This brought about the necessity for surgical operations dangerous for the patient and with long use of radiological apparatus for the verification of the two osseous stumps.

In 1945 Roger Anderson in the United States (U.S. Pat. No. 2,477,562) proposed an operating table in association with a device having pins going through for the reduction of the fracture, which however constrained the patient to a long period of immobility, with all the undesirable resulting consequences.

In 1976 a group of researchers of the French Institute ISERM & CERCA (FR-A No. 2,338,692) proposed an apparatus provided with movable clamps along two parallel guides and with jaws with a spring held by friction. However, the apparatus was cumbersome and complex, requiring complex investigations and manipulations to reduce the fracture contemporaneously in the two vertical and horizontal planes.

In 1978 the american Richard Frederick Kronner (FR-A No. 2,439,002) proposed an apparatus to reduce and immobilise the fracture which however was very heavy, of great encumbrance and difficulty to set up.

In 1979 a group of Czechoslovakian researchers (CH-A No. 738,390) proposed a device to reduce the fracture provided with elements slidable on parallel guides. The locking clamps are very simple and do not permit variations in inclination and length, as a result of which there is little possibility of reducing the fracture.

In 1981 Rudolf Kleining (DE-A No. 3,118,397) proposed an over-simplified device in which there was complete lack of a pivot for external adjustment, as a result of which it was impossible to reduce a fracture after having placed the apparatus in operation. Because of this, it could only be used for fractures already reduced, which did not require interventions in the apparatus after it was inserted.

Also in 1981 Juan Lazo Zbikowski (FR-A No. 2,517,535) proposed a device with screws which were absorbable and aligned, held by clamps of considerable weight and encumbrance, which did not have a very great stability of retention at a distance, and did not permit to reduce the fracture at the same time in two planes, with great harm for the patient and operators exposed for much time to radiological emissions for verifying the alignment of the skeletal stumps.

In 1981 the present applicants Castaman and Borghettini (IT-A No. 85609/81) proposed a device for the stabilization of the fracture of long bones which offers an easy possibility of reduction in various planes, an optimum mechanical stability, a wide versatility resulting at the same time in a low weight and low encumbrance, with notable advantages for the patient and for the surgeon.

The present application describes a device which is improved with respect to the previous invention, both with respect to the manner of fixing the bone-traversing pins to the structure of the carrier bar, and with respect the component parts of the bar itself, in such a manner as to increase the stability of the apparatus during use and the possibility of adjustment of the parts of the same during the operation of applying it to the limb of the patient.

One of the inconveniences which occur in practice resides in the difficulty of guaranteeing a secure position at the time of positioning of the various metal pins, which may be threaded, at the time of inserting them into the individual fragmented bones, for the purpose of holding them in position, up to the time when they are joined. A second inconvenience, which occurs sometimes in the use of the abovementioned locking apparatus (IT-A No. 85609/81) is due to the fact that at the point of connection of the parallel portion with the threaded portion, the bar carrying the pin which has passed through the bone is rotated, with grave consequences on the healing of the patient.

All of these inconveniences are eliminated with the adoption of the apparatus improved in accordance with the invention, because the system for locking of the bearing elements, which fix the pins passing through the bones to the carrier bar of the apparatus is made by means of a stirrup and washer both having a deformable lining. Further, the parallel portion of the track of the carrier bar has a rough surface which guarantees an almost immovable fixture of the pins.

The curvilinear connection between the tracked portion and the threaded portion of the carrier bar almost completely eliminates the possibility of rotation, following the usual manipulations which occur once the apparatus is put to use, guaranteeing the maximum security during use of the apparatus.

Other improvements relate to the particular ovoidal shape of the threaded portion of the carrier bar which permits to orient, in torsional manner, and in the most suitable way, the two parts which constitute the carrier bar itself, as required by the particular exigencies of the patient.

A further feature of novelty is constituted by the fact that only one of the two carrier bars is fixed to the intermediate pivot by an adjustable telescopic sysetm, whilst the other forms a unitary body with the intermediate stirrup. This considerably simplifies the manipulation of adapting the apparatus to the specific case of the patient on which it is applied and also increases the entire stability of the apparatus.

In another embodiment the apparatus is constructed with a series of pins disposed on one plane perpendicular to a second series of pins, which lends itself to the employment of the apparatus in epiphytal fractures, because it permits the placing of a series of pins, traversing the epiphysis, in a plane which is substantially perpendicular to that of the series of pins penetrating through the diaphyses.

These and other features of the invention will be better described in the following and illustrated in the accompanying set of drawings, wherein:

FIG. 2 represents a profile view of the same;

FIG. 3 is a front view the point of connection between the threaded portion and the guiding tracked portion of the rod carrying the pins;

FIG. 4 is a cross section taken along the line IV—IV of FIG. 3;

FIG. 5 represents a side view, with the parts shown separately, of the locking screw of a pin.

Figure 1:
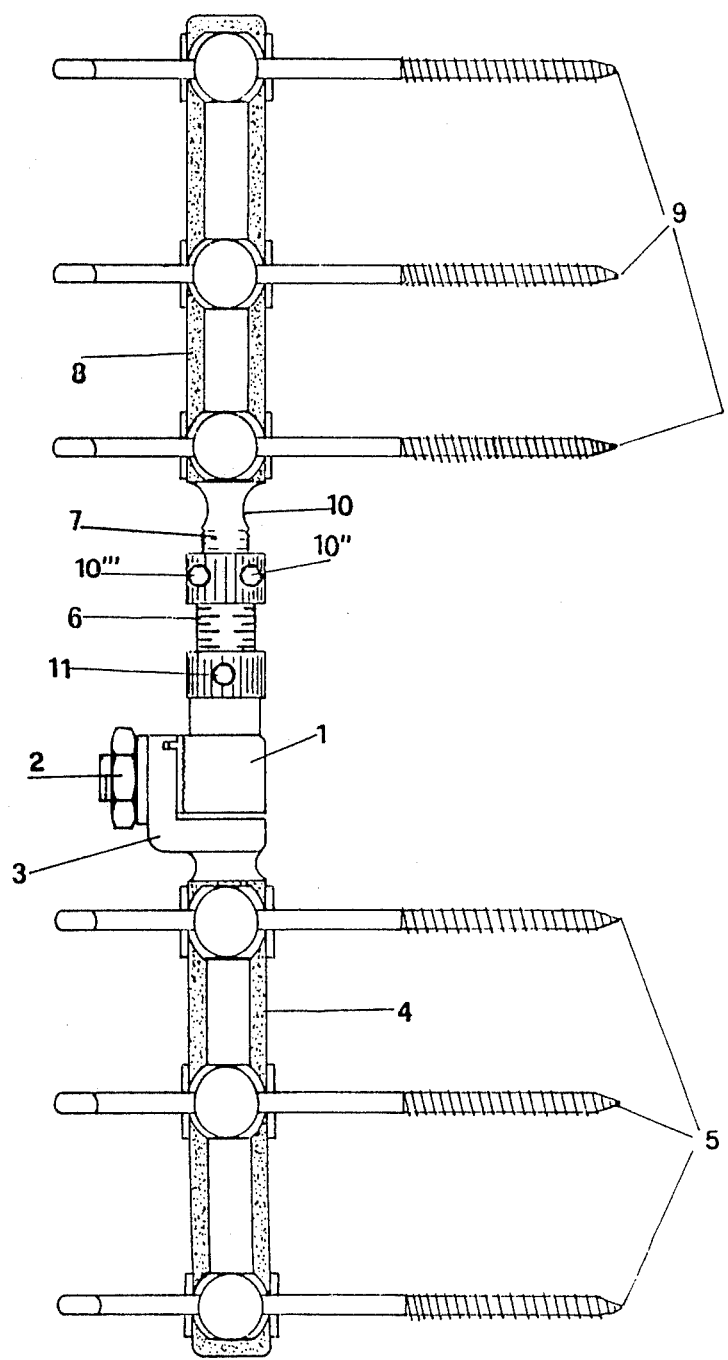
FIG. 1 (sheet 1) represents a front elevational view of an apparatus with two series of aligned pins.

The apparatus illustrated in FIGS. 1 to 4 is particularly adapted to be employed in central fractures of long bones.

This comprises a pivot block 1 which is connected, by means of the screw 2 to the bracket 3, with which is integral the tracked bar 4 carrying the pins 5.

On the side opposite to the block 1 there is fixed the threaded socket 6, on which in its turn there is screwed the threaded stud 7, integral with the second tracked bar 8 carrying the pins 9.

It will be seen that the screw 7 (FIGS 3 and 4) has an ovoidal section in which the threads are limited to the two opposed sections 10 and 10', while on one of the two curved surfaces, but not threaded, there rest the headless threaded screw 10" and 10'" having a shaping of the head which does not permit locking.

Two screws with mutually convergent axes guarantee alone an optimum locking, and the two opposite screws can be omitted when not needed.

Analogously the screw 11 guarantees an optimum pressure on the flat central non threaded portion of the socket 6, which in this manner remains rigidly fixed to the pivot block 1.

On the flat roughened surfaces of the carrier bars 4 and 8 there are fixed, as has been mentioned, the respective pins 5 and 9, by means of the screw 12 fixed to the respective bar by means of the nuts 13, by means of the stirrup 14 and the washer 15, both provided with a layer of deformable material, respectively 14' and 15', which comes to bear on the roughened surfaces 4 and 8 of the slotted portions of the carrier bars.

The normal metallic washer 16 bears directly on the underside of the nut 13, assuring a firm locking of the latter on the stirrup 14.

Figures 6, 7:
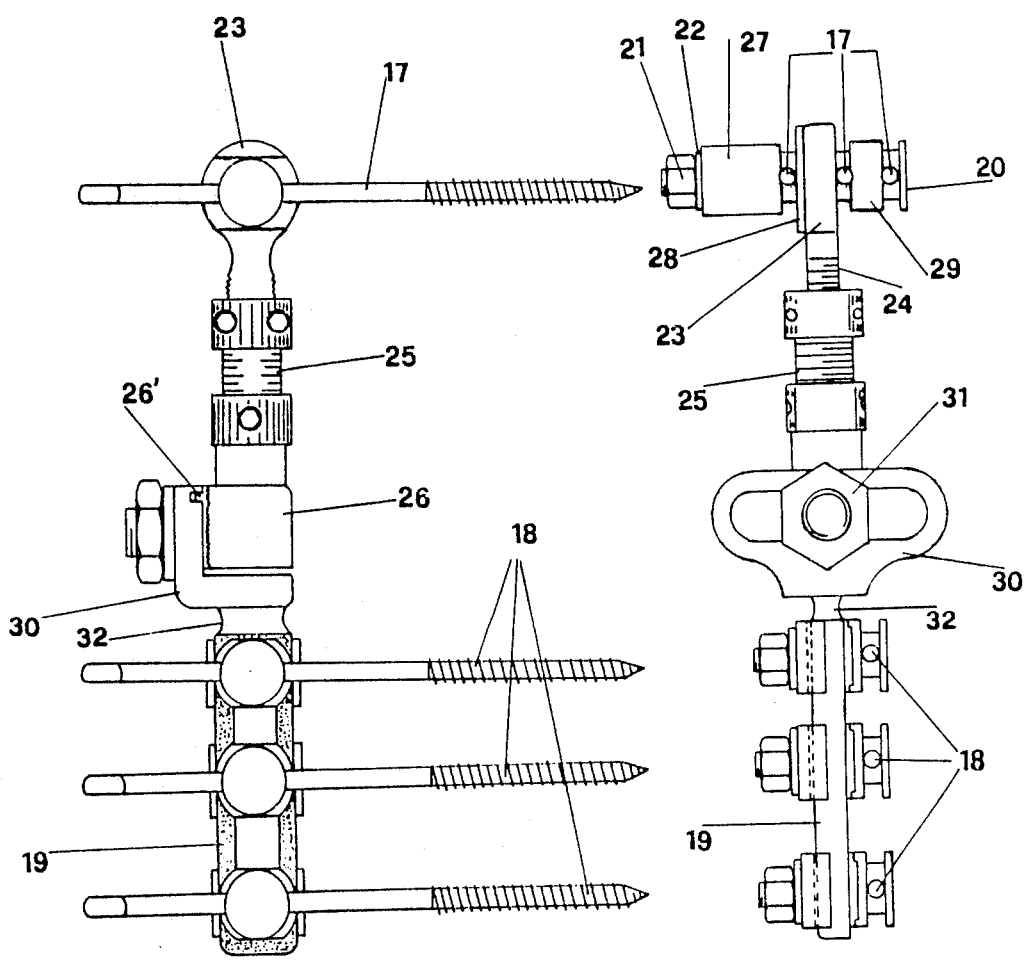
FIG. 6 (sheet 2) represents, an elevational view of a second form of construction of the apparatus of the invention, intended for epiphytal joints.
FIG. 7 represents a side view of the same.

In FIGS. 6 and 7 it will be seen that the series of pins 17 is disposed in a plane which is perpendicular with respect to the series of pins 18, because this second form of construction of the apparatus is intended for the stabilization of epiphytal osseous fractures.

In this case, the carrier bar of tracked construction is single and is shown with the reference numeral 19. This bar is intended to carry the pins 18 for insertion into the osseous diaphyses, while the pins 17 intended for insertion into osseous epiphyses are simply fixed to the drilled shank 20, provided with a nut 21 and washer 22, which locks the pin 17 to the socket 23 of the threaded portion 24 of the carrier bar, in its turn fixed by the socket 25 and pivot 26, to the tracked portion 19 of the carrier bar.

In the first case there are provided simple channels, with parts of circular section, formed on the block 27, on the washer 28 and on the block 29 disposed facing the pins 17. The pins 18 are, on the contrary, fixed to the tracked portion 19 of the carrier bar, by means of bolts with nuts, washers and stirrups, provided with a deformable coating, analogously to what has been described in the first form of construction of the apparatus illustrated in FIGS. 1 to 5.

Also in this case however, while the pins 17 are connected to the pivoting element 26, by means of the socket 25 of adjustable position, so as to permit a lengthening of the distance between epiphysis and diaphysis, the tracked portion 19 is connected to the stirrup 30, which is in its turn fixed by means of the nut 31 to the pivot 26, through the neck 32, of curvilinear shape, the shaping of which is such as to eliminate the possibility of rotation which would be extremely dangerous for the recovery of the patient.

Figures 8, 9:
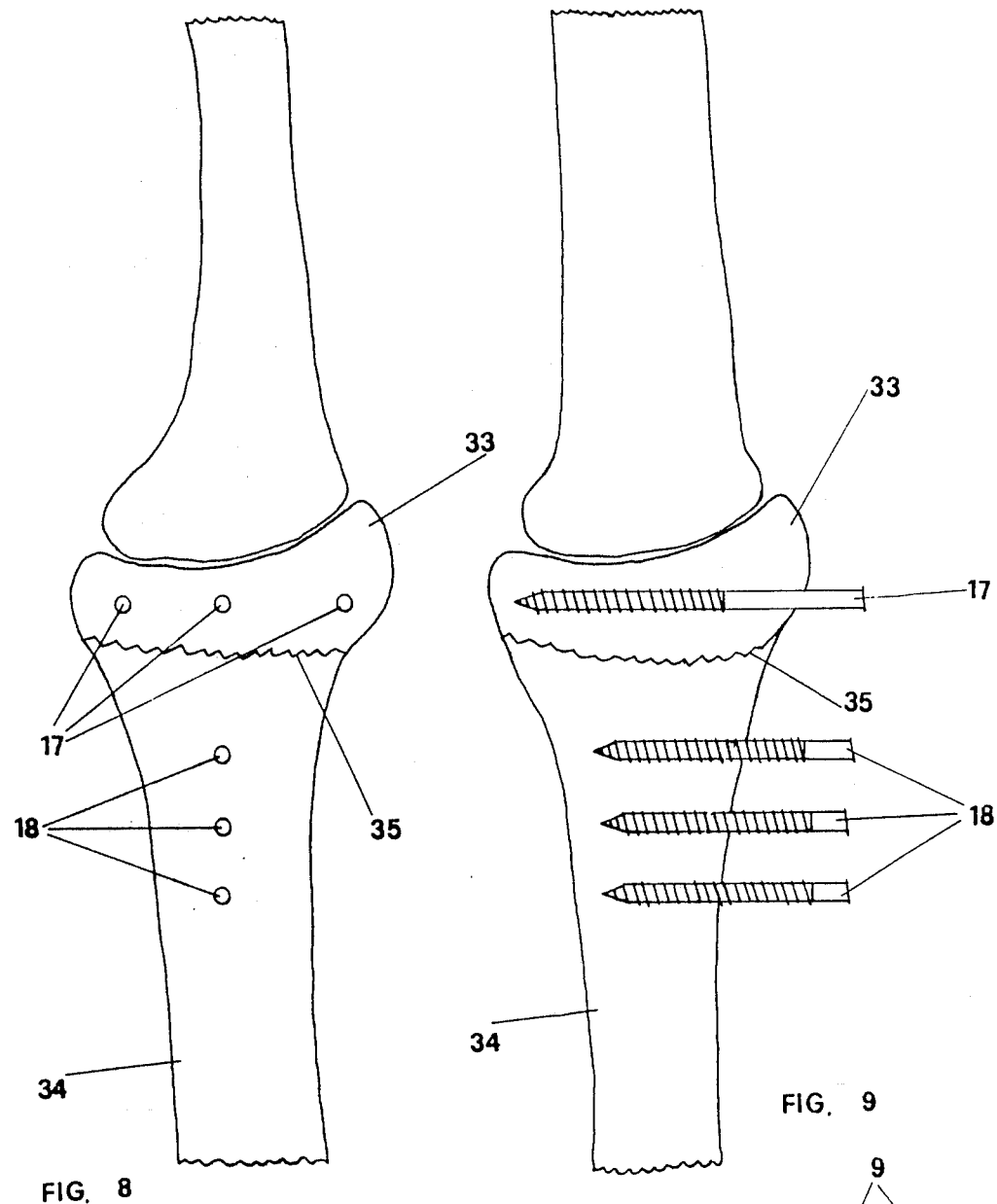
FIG. 8 (sheet 3) represents schematically a bone joint with indication of the points of insertion of the pins in the apparatus for epiphytal joints according to FIGS. 6 and 7.
FIG. 9 represents a side view of the same.
Figure 10:
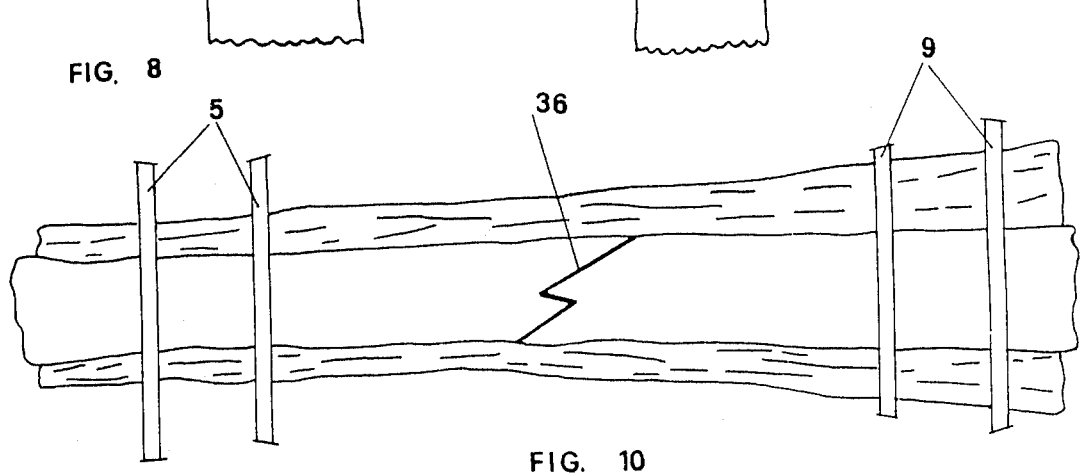
FIG. 10 represents schematically and in side view a bony structure with indication of the points of passage of the pins, in the case of intermediate bone fracture.

In FIGS. 9 and 10 there are shown the points of insertion of the pins 17, into the epiphysis 33, whilst the pins 18 penetrate into the diaphysis 34 of the bone, the line of fracture of which is shown schematically by the line 35.

In the case of fracture of a central portion of a long bone, the pins 5 and 9 (FIG. 10) are inserted at opposite parts with respect to the line of intermediate fracture 36.

It is to be noted that the apparatus now described could be usefully employed also for artificial lengthening of the joints, by means of periodical adjustment of the position of the respective threaded sockets 6 and 25, which brings about the resultant increase of the distance between the truncated bones and successive regrowths of the same, in accordance with the by now well known treatments in the field.

Naturally this will be facilitated by the presence of means of adjustment 10", 10'" and 11 (FIG. 1) which, when loosened, permit the lengthening of the apparatus by simple rotation of rotating means or by rotation in its turn of the socket 6 and successive stabilization for a successive period of regrowth of the osseous callus.

Naturally, the constructive features of details of the apparatus, such as for example the number of pins or the position thereof, the dimensions of the various parts and the particular finish, can assume various shapes and aspects with respect to those now described and illustrated on the set of accompanying drawings, provided that the essential features, set out in the successive claims, remain the same, without thereby exceeding the scope of the invention.

What is claimed is:

1. An external device for use in orthopedic surgery for fixing pins adapted to be secured to bone fragments, comprising a pivot block (1, 26), at least one carrier bar (4, 8, 19) fixed to said pivot block, bone-traversing pins adapted for insertion into bone fragments, at least one first element (12) for securing the pins to said carrier bar, said carrier bar having in part a rough surface, means for locking said first element (12) to said carrier bar, said means consisting of a stirrup (14) and a washer (15) located on either side of said carrier bar, said stirrup and said washer having at least the surface in contact with said rough surface of said bar covered with a deformable lining, a second element (13) for clamping said stirrup and said washer to said first element (12).

2. The device according to claim 1 wherein said first element (12) is a screw and said second element is a nut.

3. The device according to claim 1 which comprises two carrier bars, each carrier bar comprises a tracked structure, one tracked structure has a stud (7) connecting said tracked structure to said first element and a section of said connecting portion has reduced cross sectional area, wherein said stud (7) has threaded portions (10, 10¹) having opposed flat portions, said pivot block is fixed to a socket (6), said socket has a threaded portion, the threads of said stud (10, 10¹) being operatively engageable with the threads of said socket.

4. The device according to claim 3 wherein said socket has an external portion adapted to be connected to said pivot block.

5. The device according to claim 1 which comprises one carrier bar (19), said carrier bar (19) carries an alternate first element (20) for securing a plurality of pins (17) generally perpendicular to the longitudinal axis of said carrier bar.

6. The device according to claim 5 wherein the pivot block (26) has a socket (25) fixed thereto, said carrier bar has a threaded portion (24) and has an eye (23) to receive said alternate first element, said threaded portion (24) being fixed to said eye (25).

* * * * *